US00PP29855P3

(12) United States Plant Patent
Jernigan

(10) Patent No.: US PP29,855 P3
(45) Date of Patent: Nov. 20, 2018

(54) ***GARDENIA* PLANT NAMED '4MARIAJ01'**

(50) Latin Name: *Gardenia jasminoides*
Varietal Denomination: 4MARIAJ01

(71) Applicant: Brian J. Jernigan, Dearing, GA (US)

(72) Inventor: Brian J. Jernigan, Dearing, GA (US)

(73) Assignee: Center for Applied Nursery Research, Inc., Dearing, GA (US)

( * ) Notice: Subject to any disclaimer, the term of this patent is extended or adjusted under 35 U.S.C. 154(b) by 0 days.

(21) Appl. No.: 15/732,486

(22) Filed: Nov. 16, 2017

(65) Prior Publication Data

US 2018/0084690 P1 Mar. 22, 2018

(51) Int. Cl.
*A01H 5/02* (2018.01)

(52) U.S. Cl.
USPC ..... Plt./255
CPC ..... *A01H 5/02* (2013.01)

(58) Field of Classification Search
USPC ..... Plt./255
See application file for complete search history.

*Primary Examiner* — Annette H Para
(74) *Attorney, Agent, or Firm* — James R. Holm

(57) ABSTRACT

A new and distinct *gardenia* plant named '4MARIAJ01' particularly distinguished by flowers that are double-flowered with an early flowering habit, upright, dark green growth with a dense branching habit and increased flower production compared to other standard large growing double-flowered cultivars, and plants having uniform growth under commercial production practices, is disclosed.

4 Drawing Sheets

Figure 1:
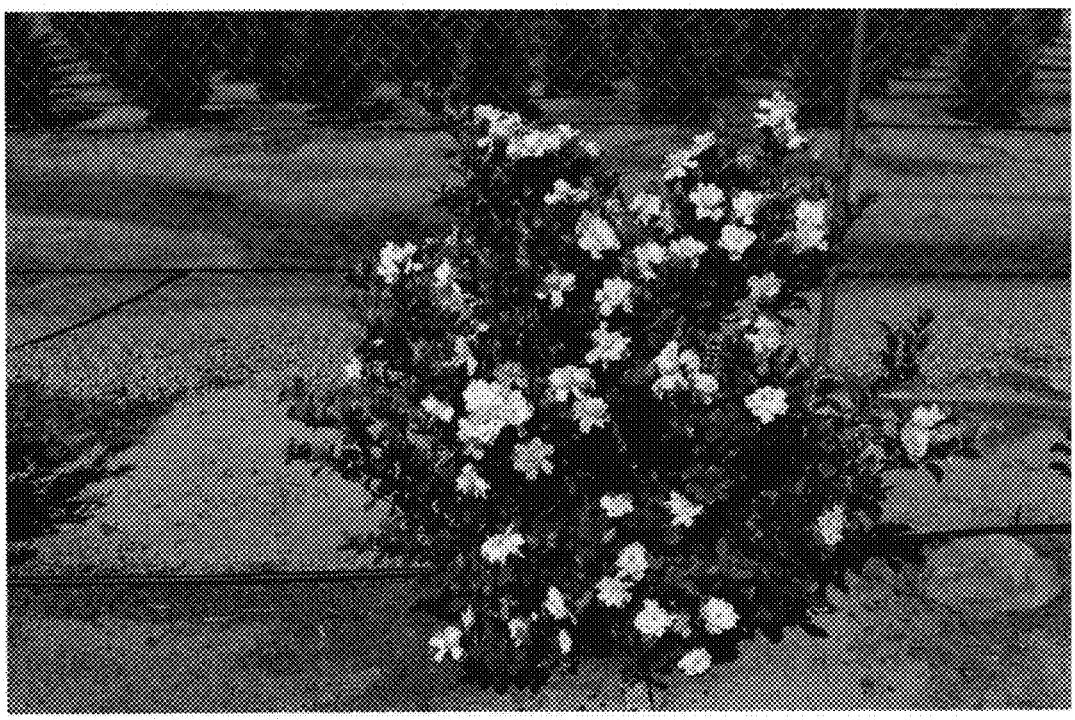

Genus and species: *Gardenia jasminoides.*
Variety denomination: '4MARIAJ01'.

BACKGROUND OF THE NEW PLANT

The present invention comprises a new and distinct variety of *gardenia* plant, botanically known as *Gardenia jasminoides*, and hereinafter referred to by the variety name '4MARIAJ01'. This new *gardenia* plant originated from an open pollination conducted in 2009 in Dearing, Ga. between an unknown female *gardenia* plant and an unknown male *gardenia* plant. The objective of the breeding program was to create a new *gardenia* plant with an early blooming habit, double-flowered, compact growth habit, easy-to-grow, and plants exhibiting cold hardiness.

Approximately 1400 progeny seeds resulting from said open pollination were planted in 2009. In 2010, progeny seedlings were planted in 2.5 inch liner cups and then in 2011 progeny seedlings were planted in 1-gallon containers. In 2013, progeny seedlings were planted in 3-gallon containers, inoculated with *Phytophthora cinnamomi*, and grown to evaluate disease response and production characteristics. The new variety was selected by the inventor as a single plant within said progeny in a controlled environment in Dearing, Ga. The new variety was selected based on its response to drought stress, disease, cold hardiness, and unique flowering and growth characteristics. '4MARIAJ01' was first reproduced asexually by vegetative semi-softwood stem cuttings in October 2013 in Dearing, Ga. '4MARIAJ01' has been found to retain its distinctive characteristics and has been found to be stable and reproduce true-to-type through two successive generations of asexual reproduction by vegetative semi-softwood stem cuttings.

Plant Breeder's Rights for this variety have not been applied for. '4MARIAJ01' has not been made publicly available or sold anywhere in the world prior to the effective filing date of this application.

SUMMARY OF THE INVENTION

The new *gardenia* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *gardenia* variety when grown under normal horticultural practices in Dearing, Ga. The combination of these characteristics distinguishes '4MARIAJ01' as a new and distinct variety of *gardenia:*

1. Flowers that are double-flowered with an early flowering habit;
2. Upright, dark green growth with a dense branching habit and increased flower production compared to other standard large growing double-flowered cultivars; and
3. Plants having uniform growth under commercial production practices.

DESCRIPTION OF THE PHOTOGRAPHS

This new *gardenia* is illustrated by the accompanying photographs which show the overall plant habit including flowers and foliage of the plant. The colors shown are as true as can be reasonably obtained by conventional photographic procedures. The photographs are of 3.6 to 4-year-old plants and 8-year-old plants grown in the ground and in 3-gallon containers in Dearing, Ga. The photographs were taken in May 2017 in Dearing Ga. under natural light. Colors in the photographs may differ slightly from the color values cited in the botanical description which accurately describes the colors of the new variety.

FIG. 1. shows the original seedling and its overall habit, including flowers and foliage.

Figure 2:
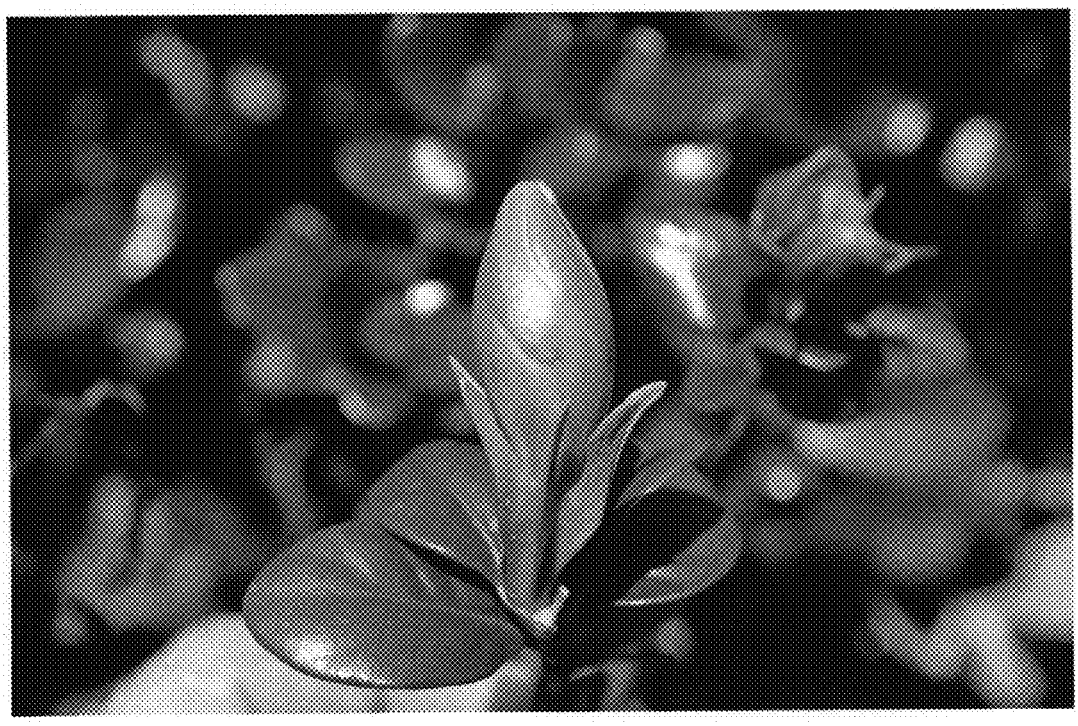

FIG. 2. shows a typical flower bud.

Figure 3:
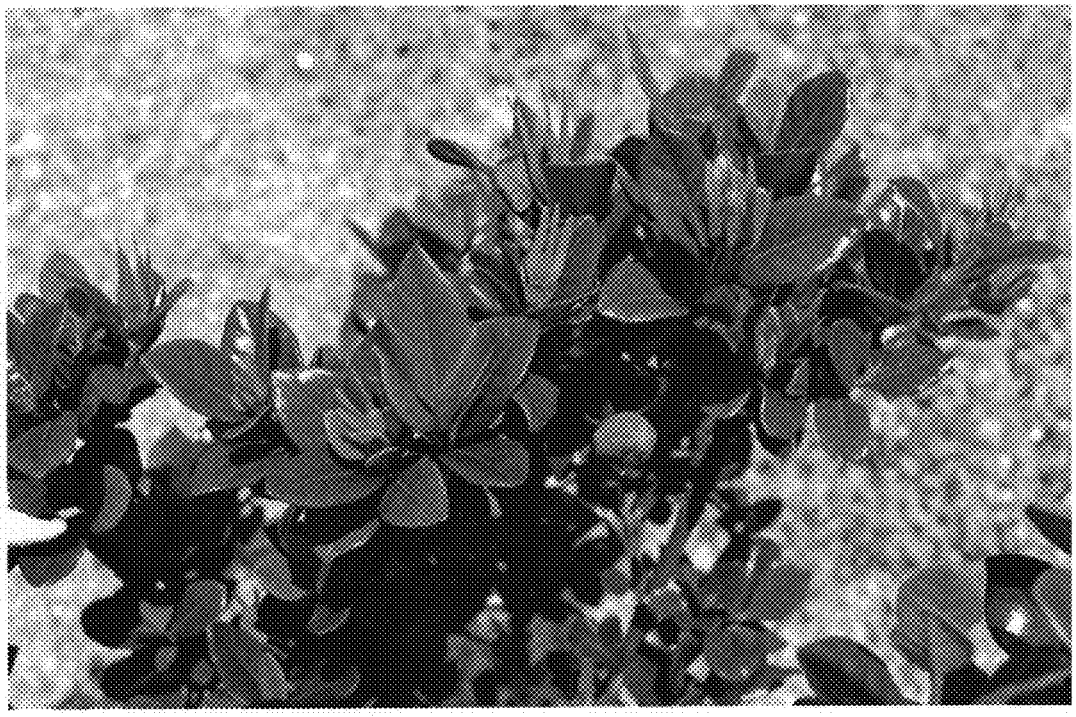

FIG. 3. shows typical foliage and flower buds.

Figure 4:
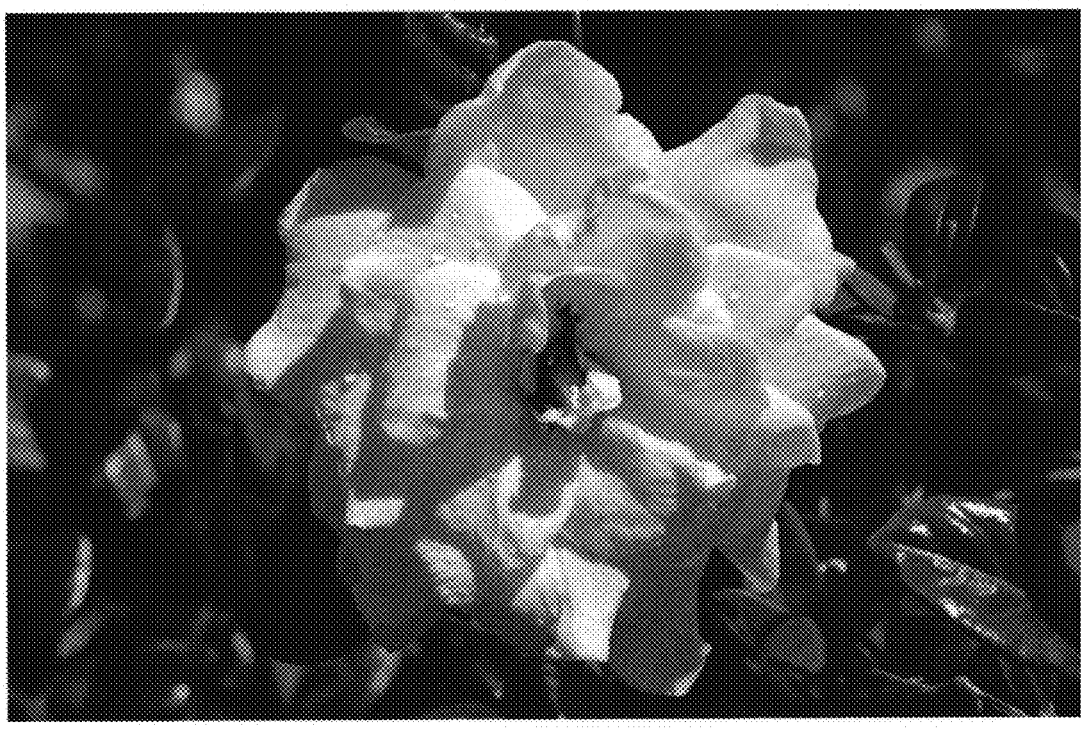

FIG. 4. shows a close up of a mature flower.

DESCRIPTION OF THE NEW VARIETY

In the following description, color references are made to The Royal Horticultural Society Colour Chart, Sixth Edition, except where general terms of ordinary dictionary significance are used.

The following observations and measurements describe plants grown in the ground and in 3-gallon containers when grown outdoors under a natural photoperiod in full sun in Dearing, Ga. Detailed descriptions were taken in 2016 and 2017 from approximately 4-year-old plants grown from single vegetative semi-softwood stem cuttings. Measurements and numerical values represent averages of typical plant types.

DETAILED BOTANICAL DESCRIPTION

Classification:

*Family*.—Rubiaceae.

*Botanical.—Gardenia jasminoides.*

*Common.—Gardenia.*

*Denomination.*—'4MARIAJ01'.

Parentage:

*Female or seed parent*.—Unknown.

*Male or pollen parent*.—Unknown.

Propagation:

*Type*.—Vegetative semi-softwood stem cuttings.

*Time to initiate roots*.—10 to 20 days.

*Time to produce a rooted young plant*.—5 to 6 months, a cutting placed in rooting media in approximately September to October will be rooted and ready to pot in approximately February to March the following year, rooting time is shorter during warmer months.

Root description: Fibrous.

Plant description:

*Plant type*.—Evergreen shrub.

*Growth habit*.—Densely upright, mounding.

*Height*.—93.0 cm after 4 years of growth and 128.0 cm after 8 years of growth.

*Plant spread*.—72.0 cm after 4 years of growth and 132.0 cm after 8 years of growth.

*Growth rate*.—15.0 cm to 22.0 cm per year depending on environmental conditions and plant's age, growth rate slows as plants mature.

*Plant vigor*.—Vigorous when young, vigor slows as plants mature.

*Branching habit*.—Freely branching.

*Primary branches* (*one year or older*).—Length: 22.0 cm per year. Diameter: 0.6 cm at one year of age, 1.8 cm at four years of age. Strength: Pliable during the first year's growth and becoming stiff the second year. Color: Mature branches: Green 138B, grey-green 190C and brown N200A. Young branches: Brown 200A, grey-brown N199B, and yellow-green 147D. Texture: No pubescence, some exfoliation.

*Lateral branches* (*less than one year old*).—Length: 10.8 cm per flush. Diameter: 0.6 cm. Strength: Flexible. Aspect: 10 to 60 degree angles from other stems. Texture: Setulose pubescence. Color: Immature branches are green 143A and yellow-green 144A, and maturing to green 143B and then grey-brown 199B and N199B. Internode length: 3.03 cm.

Foliage description:

*Leaf type*.—Simple.

*Leaf arrangement*.—Primarily opposite with some whorled leaves, 2 per node, rarely 3 per node.

*Average mature leaf size*.—Length: 4.43 cm. Width: 2.58 cm.

*Mature leaf shape*.—Obovate.

*Leaf apex*.—Obtuse.

*Leaf base*.—Crunate.

*Leaf attachment*.—Petiolate with persistent sheathing stipules at the apex of the node.

*Leaf margin*.—Entire.

*Internode length*.—2.78 cm.

*Leaf texture*.—Upper surface: Glabrous, waxy. Bottom surface: Glabrous.

*Leaf color*.—Young leaves: Upper surface: Yellow-green 144A. Lower surface: Yellow-green 145B. Mature leaves: Upper surface: Green 139A. Lower surface: Yellow-green 146B.

*Leaf venation*.—Type: Pinnate. Color: Upper surface: Yellow-green 144A. Lower surface: Yellow-green 145B.

Flower description:

*Bloom period*.—Primary bloom period is typically May in Dearing, Ga., blooming occurs sporadically through summer and into fall.

*Type*.—Perfect flower, complete and near complete.

*Arrangement*.—Solitary flower at apex of stems and occasionally at leaf axils.

*Peduncle*.—Length: 0.5 cm. Diameter: 0.3 cm. Color: Yellow-green 144A. Texture: Glabrous. Strength: Slightly pliable, breakable with force.

*Height* (*depth*).—3.0 cm from attachment to stem.

*Diameter*.—8.5 cm.

*Facing direction*.—Outward.

*Persistence*.—Self-cleaning.

*Fragrance*.—Strong pungent *gardenia* fragrance.

*Flower tube*.—Length: 1.7 cm. Width at widest point: 1.5 cm. Width at narrowest point: 0.8 cm. Texture: Setulose pubescence.

*Petals*.—Arrangement: 3 rows of petals with 1 row of petaloids. Length: Outer row: 3.6 cm. Second row: 3.5 cm. Third row: 3.0 cm. Fourth row: Petaloids measuring 2.5 cm in length from point of fusion with the flower tube with some smaller, irregular petaloids present. Width: Outer row: 3.4 cm. Second row: 2.8 cm. Third row: 2.4 cm. Fourth row: Petaloids measuring 1.7 cm in width with some smaller, irregular petaloids present. Apex: Unevenly rounded. Base: Fused tube. Shape: Obovate. Margin: Entire, slightly wavy and reflexed with age. Quantity: 6 per row. Texture: Smooth, glabrous. Color: Outer surface at maturity: White NN155D. Inner surface at maturity: White 155C with an area on the outer petals of yellow-green 144C. Upper and lower surfaces at fading: Yellow 11A and 11C.

*Buds*.—Shape: Oblong. Length: 3.6 cm. Diameter: 1.5 cm. Color: Yellow-green 144A. Texture: Glaborous on the swollen area of the petals at the apex.

*Calyx/sepals*.—Quantity of sepals per flower: 6. Calyx arrangement: Star-shaped. Sepal shape: Lanceolate and fused to the base. Length: Calyx is 1.5 cm with sepals extending 1.5 cm beyond calyx. Width: 1.2 cm at the base of the flower tube, sepals measure 0.3 cm in width at the point of fusion to the calyx. Apex: Acute. Base: Fused. Margin: Entire. Texture: Glabrous. Color (both inner and outer surfaces): Yellow-green 144A.

Reproductive organs:

*Stamens*.—Quantity: Petaloid, varying in presence, 0 to 6 with 6 fused petaloid stamens most commonly present. Length: 2.5 cm. Width: 1.7 cm. Anthers: Aspect: Wavy, curving and fused with the petaloids. Length: 0.8 cm. Width: 0.15 cm. Color: Greyed-orange 164A. Pollen: Amount: Moderate. Color: Yellow 6D.

*Pistils*.—Quantity: 1 per flower. Length: 2.7 cm. Style: Length: 1.0 cm. Color: Green-white 157D. Stigma: Shape: Obovate with 3 to 4 lobed irregular, stigma measure 1.0 cm in length and 0.6 cm in width. Color: Yellow 6D. Ovary: Type: Inferior within calyx cup. Length: 0.5 cm. Diameter: 0.5 cm.

Cold tolerance: Hardy to USDA zone 7 with current evaluations of cold hardiness in USDA zone 6.

Disease and pest tolerance: Tolerance to root diseases has been observed, but not under controlled conditions. Susceptible to insect pests common to *gardenia*, such as scale and whitefly.

Fruit and seed set: None observed.

Drought tolerance: Tolerance to periodic drought stress has been observed in container grown plants.

COMPARISON WITH KNOWN CULTIVARS

'4MARIAJ01' differs from the commercial *gardenia* variety 'BAB1183' (U.S. Plant Pat. No. 22,797) in that '4MARIAJ01' has a more compact growth habit with plants measuring 93.0 cm by 72.0 cm after 4 years of growth, whereas plants of 'BAB1183' measure 122.0 cm by 152.0 cm after 2 years of growth. Additionally, when compared to 'BAB1183', '4MARIAJ01' has tighter growth with an internode length of 3.03 cm, whereas 'BAB1183' has an internode length of 5.2 cm. Furthermore '4MARIAJ01' exhibits much smaller leaves measuring 4.43 cm by 2.58 cm, whereas leaves of 'BAB1183' measure 10.2 cm by 4.4 cm.

'4MARIAJ01' differs from the commercial *gardenia* variety 'Chuck Hayes' (U.S. Plant Pat. No. 8,755), in that '4MARIAJ01' has a growth rate of 15.0 cm to 22.0 cm per year, whereas 'Chuck Hayes' has a growth rate of 30.48 cm to 45.72 cm per year. Additionally, leaves of '4MARIAJ01' are obovate, whereas leaves of 'Chuck Hayes' are lanceolate to broad, short and obovate. Furthermore, when compared to 'Chuck Hayes', '4MARIAJ01' has an improved production consistency under a production setting in Dearing, Ga.

I claim:

1. A new and distinct variety of *gardenia* plant named '4MARIAJ01', substantially as illustrated and described herein.

* * * * *